(12) United States Patent
Baker et al.

(10) Patent No.: US 11,292,393 B1
(45) Date of Patent: Apr. 5, 2022

(54) VEHICLE SANITIZER DISPENSER

(71) Applicants: Maureen Baker, Syracuse, NY (US); Daryl Baker, Syracuse, NY (US)

(72) Inventors: Maureen Baker, Syracuse, NY (US); Daryl Baker, Syracuse, NY (US)

( * ) Notice: Subject to any disclaimer, the term of this patent is extended or adjusted under 35 U.S.C. 154(b) by 66 days.

(21) Appl. No.: 16/989,957

(22) Filed: Aug. 11, 2020

(51) Int. Cl.
| | |
|---|---|
| *B60R 7/04* | (2006.01) |
| *A47K 5/13* | (2006.01) |
| *B60R 7/08* | (2006.01) |
| *B60R 15/00* | (2006.01) |
| *A61L 2/00* | (2006.01) |

(52) U.S. Cl.
CPC ............... *B60R 7/04* (2013.01); *A47K 5/13* (2013.01); *B60R 7/08* (2013.01); *B60R 15/00* (2013.01); *A61L 2/0088* (2013.01)

(58) Field of Classification Search
CPC .. B60R 7/04; B60R 7/08; B60R 15/00; A47K 5/13; A61L 2/0088
See application file for complete search history.

(56) References Cited

U.S. PATENT DOCUMENTS

| | | | | |
|---|---|---|---|---|
| 6,428,172 | B1 * | 8/2002 | Hutzel | B60R 1/12 |
| | | | | 359/265 |
| 7,178,693 | B1 * | 2/2007 | Cutrone | A47K 5/1202 |
| | | | | 222/135 |
| 8,602,257 | B2 | 12/2013 | Godsell | |
| 9,758,101 | B2 | 9/2017 | Clair-Chalupka | |
| 2003/0117728 | A1 * | 6/2003 | Hutzel | H04N 7/181 |
| | | | | 359/838 |
| 2007/0012727 | A1 * | 1/2007 | Licari | A47K 5/13 |
| | | | | 222/167 |
| 2013/0262345 | A1 | 10/2013 | Ciavarella | |
| 2015/0250908 | A1 | 9/2015 | Maupin | |
| 2016/0080968 | A1 | 3/2016 | Jeong | |
| 2016/0221019 | A1 | 8/2016 | Bassett | |
| 2020/0383456 | A1 * | 12/2020 | Henderson | A45D 34/041 |

FOREIGN PATENT DOCUMENTS

GB    2417422    7/2006

* cited by examiner

*Primary Examiner* — Jeremy Carroll
(74) *Attorney, Agent, or Firm* — Kyle A. Fletcher, Esq.

(57) ABSTRACT

The vehicle sanitizer dispenser is a mechanical structure that is for use with a cleaning solution. An example of a suitable cleaning solution is a hand sanitizer. The vehicle sanitizer dispenser is for use with a rear view mirror of an automobile. The vehicle sanitizer dispenser mounts on the anterior surface of the rearview mirror such that the vehicle sanitizer dispenser does not interfere with the operation of the rearview mirror. The vehicle sanitizer dispenser includes a reservoir, a plurality of mirror clips, and the cleaning solution. The reservoir contains and dispenses the cleaning solution. The plurality of mirror clips attach the reservoir to the rearview mirror.

20 Claims, 6 Drawing Sheets

VEHICLE SANITIZER DISPENSER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of transportation and vehicles including fittings for vehicles, more specifically, a mirror assembly combined with other articles. (B60R1/12)

SUMMARY OF INVENTION

The vehicle sanitizer dispenser is a mechanical structure. The vehicle sanitizer dispenser is configured for use with a cleaning solution. An example of a suitable cleaning solution is a hand sanitizer that comprises an alcohol. The vehicle sanitizer dispenser is configured for use with an automobile. The automobile further comprises a rearview mirror. The vehicle sanitizer dispenser mounts on the anterior surface of the rearview mirror such that the vehicle sanitizer dispenser does not interfere with the operation of the rearview mirror. The vehicle sanitizer dispenser comprises a reservoir, a plurality of mirror clips, and the cleaning solution. The reservoir contains and dispenses the cleaning solution. The plurality of mirror clips attach the reservoir to the rearview mirror.

These together with additional objects, features and advantages of the vehicle sanitizer dispenser will be readily apparent to those of ordinary skill in the art upon reading the following detailed description of the presently preferred, but nonetheless illustrative, embodiments when taken in conjunction with the accompanying drawings.

In this respect, before explaining the current embodiments of the vehicle sanitizer dispenser in detail, it is to be understood that the vehicle sanitizer dispenser is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the vehicle sanitizer dispenser.

It is therefore important that the claims be regarded as including such equivalent construction insofar as they do not depart from the spirit and scope of the vehicle sanitizer dispenser. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
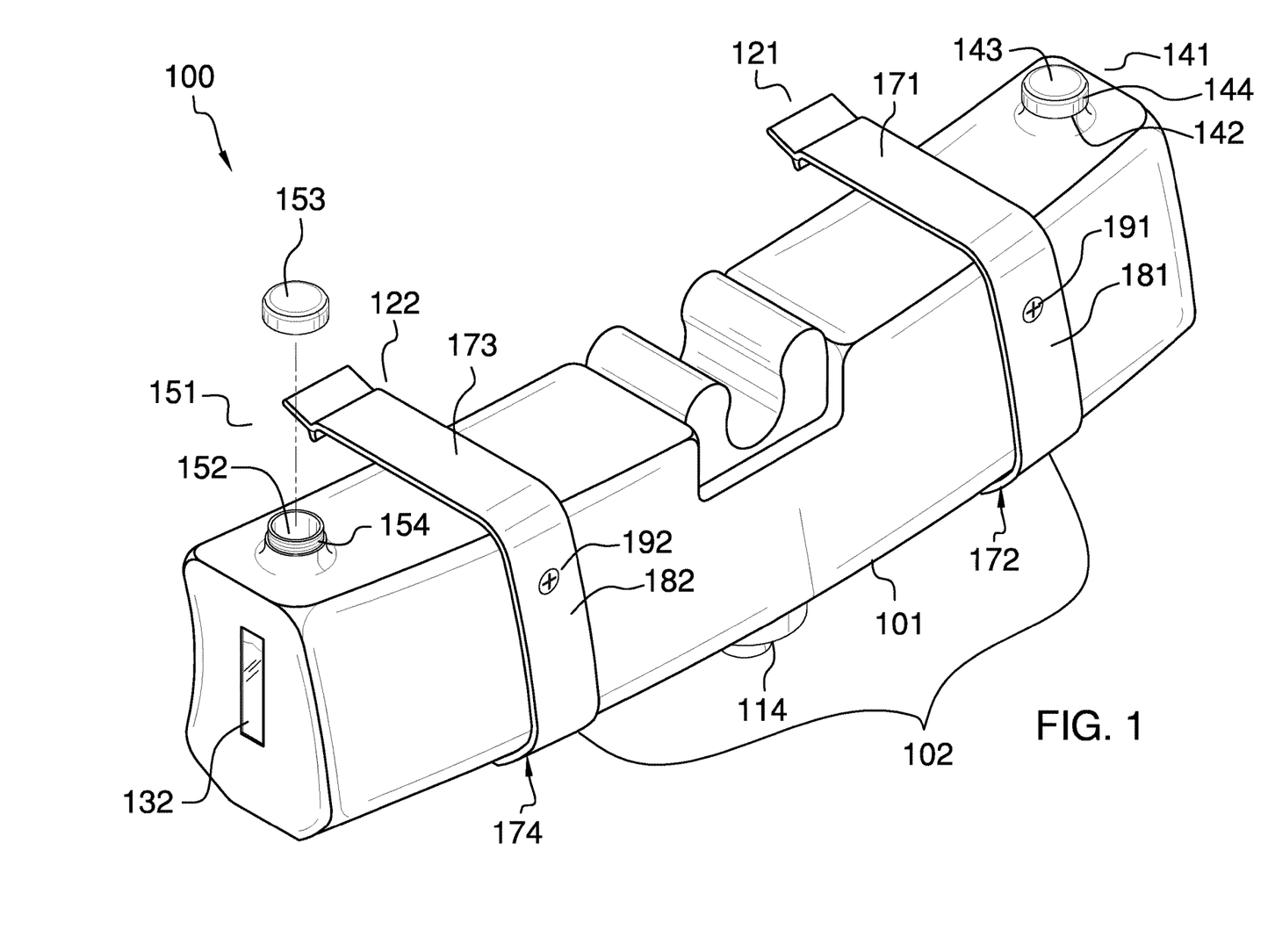
FIG. 1 is a perspective view of an embodiment of the disclosure.
Figure 2:
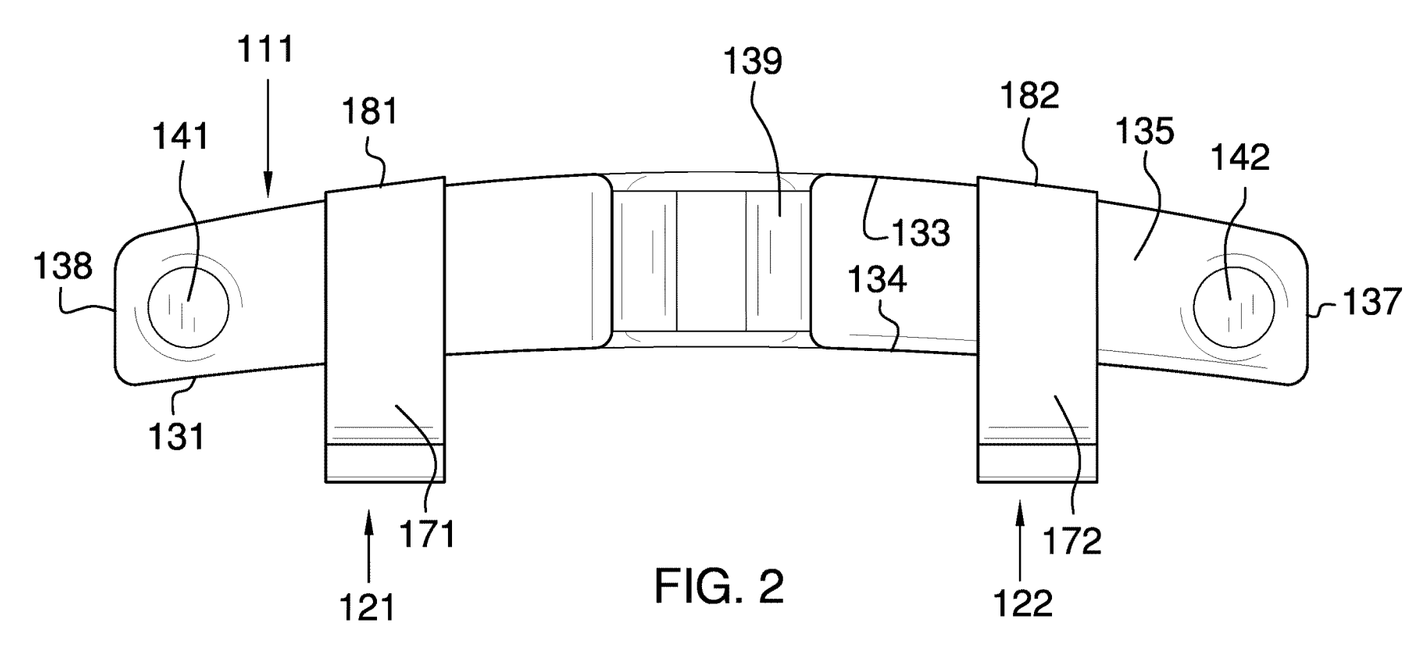
FIG. 2 is a top view of an embodiment of the disclosure.
Figure 3:
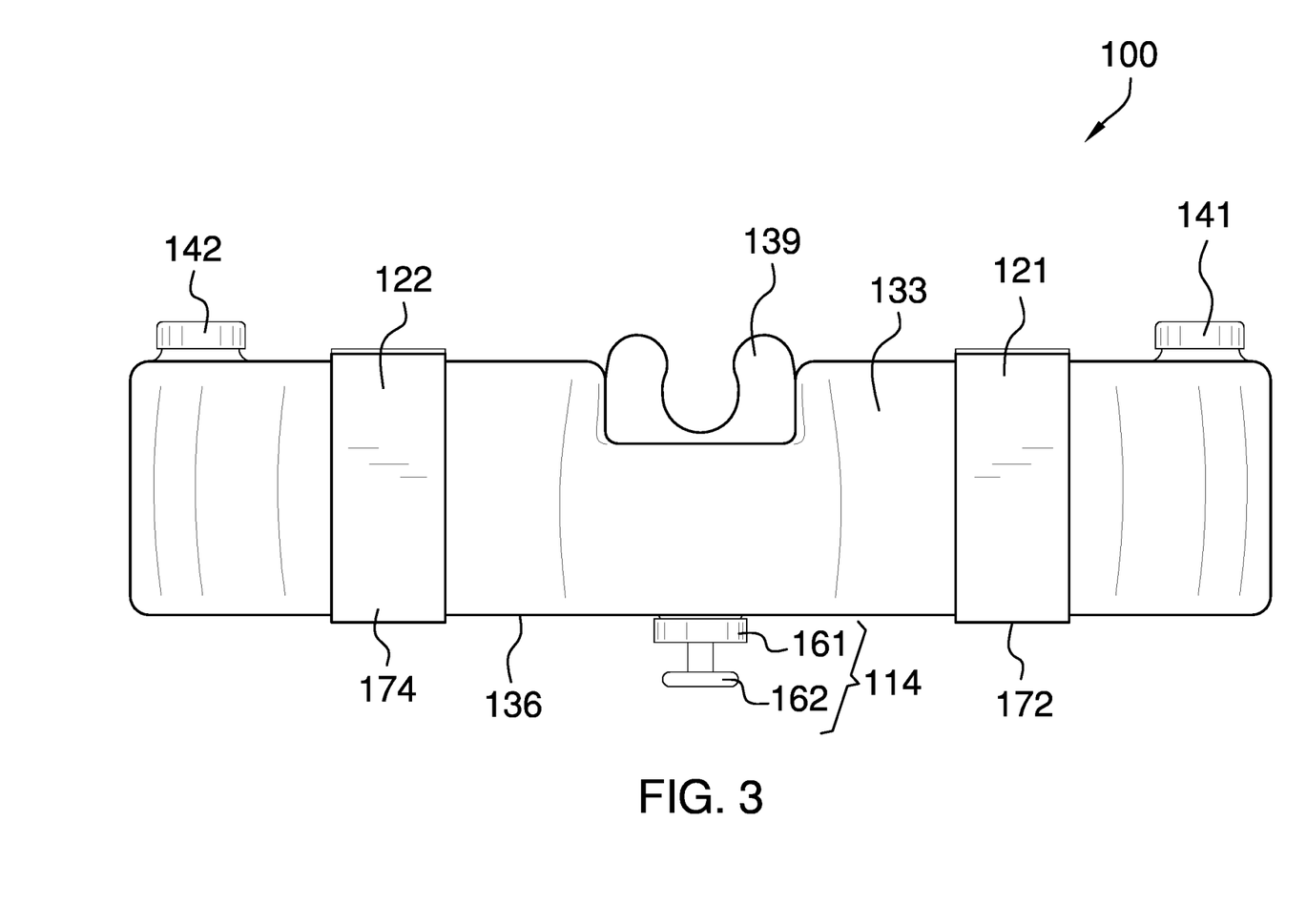
FIG. 3 is a rear view of an embodiment of the disclosure.
Figure 4:
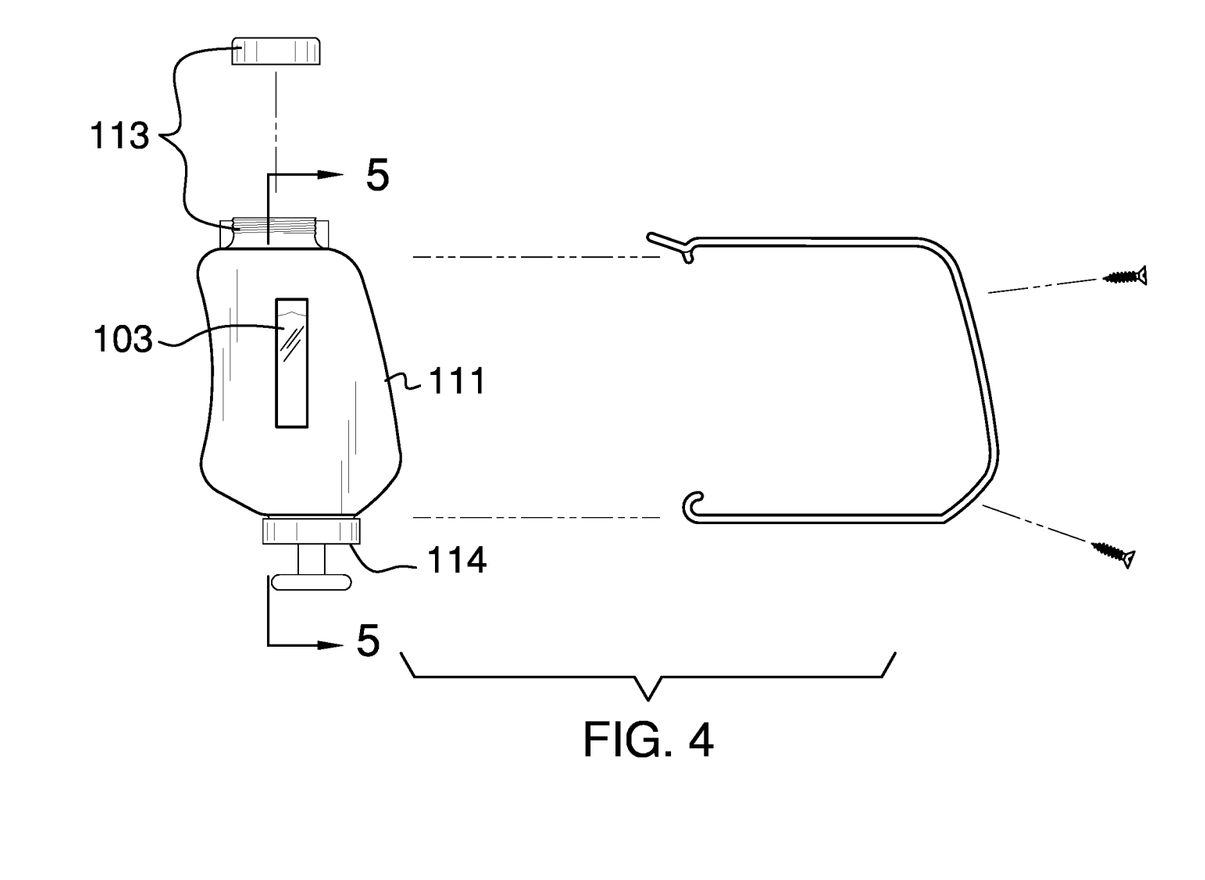
FIG. 4 is a side view of an embodiment of the disclosure.
Figure 5:
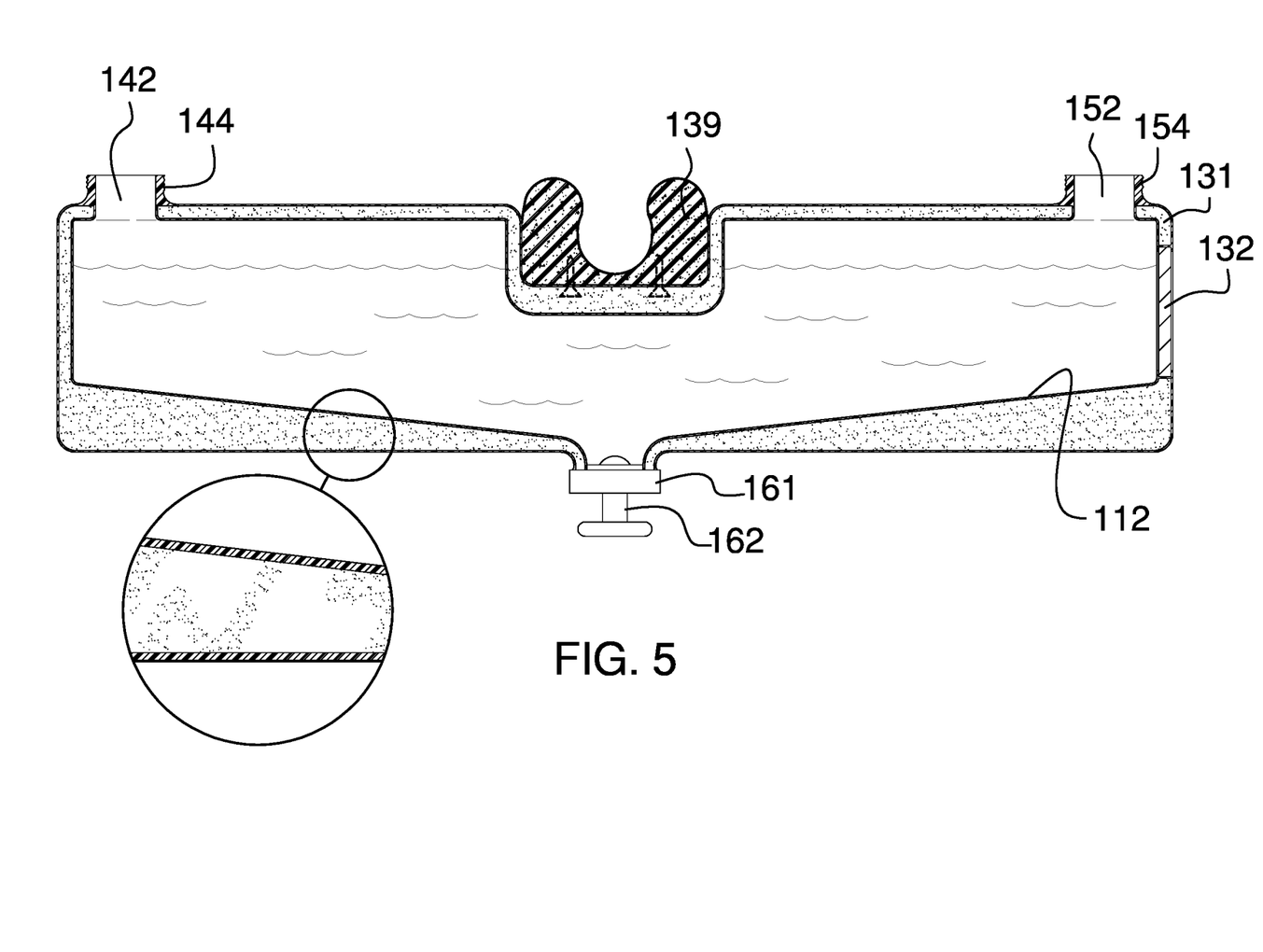
FIG. 5 is a cross-sectional view of an embodiment of the disclosure across 5-5 as shown in FIG. 4.
Figure 6:
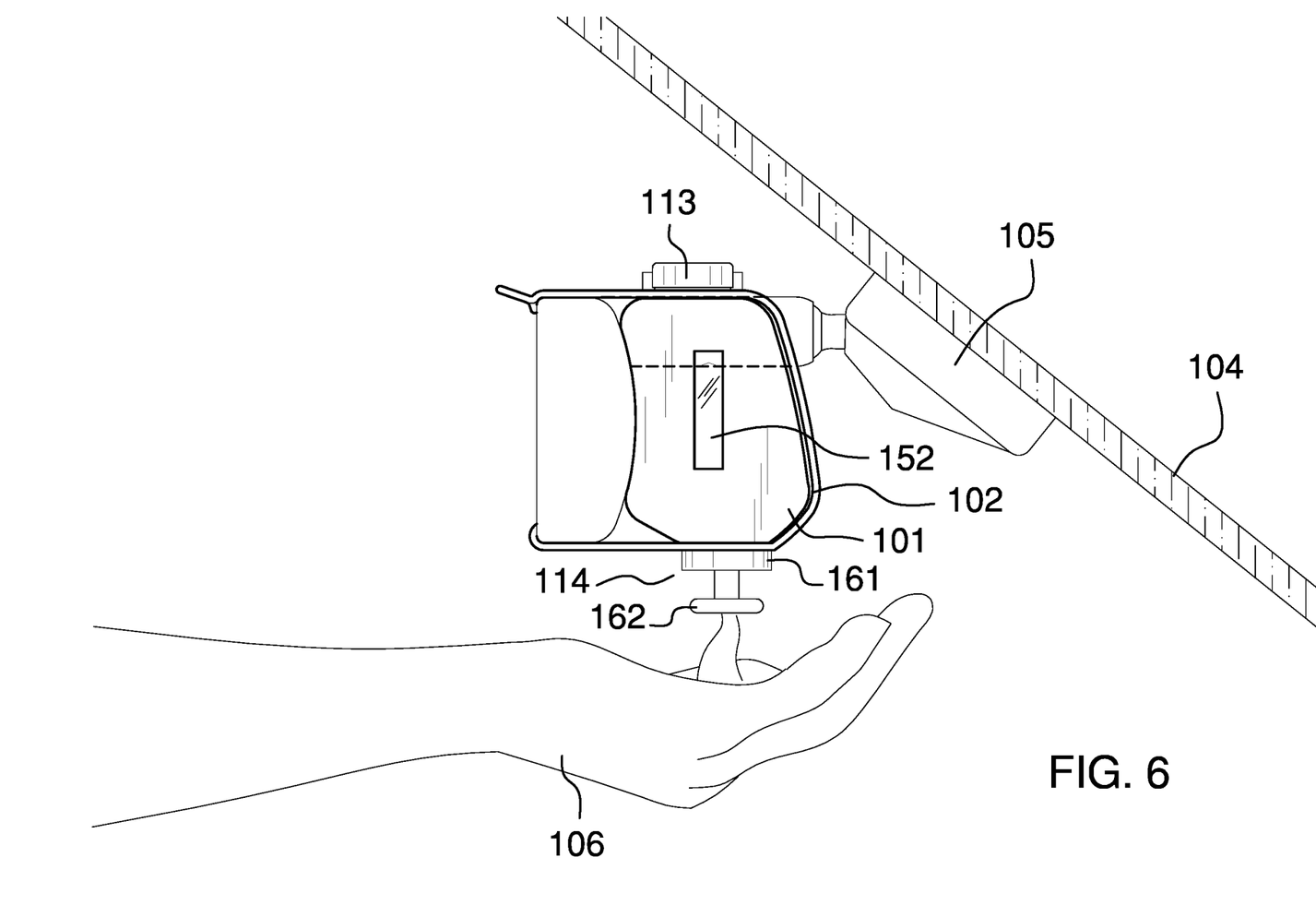
FIG. 6 is an in-use view of an embodiment of the disclosure.

Detailed reference will now be made to one or more potential embodiments of the disclosure, which are illustrated in FIGS. 1 through 6.

The vehicle sanitizer dispenser 100 (hereinafter invention) is a mechanical structure. The invention 100 is configured for use with a cleaning solution 103. An example of a suitable cleaning solution 103 is a hand sanitizer that comprises an alcohol. The invention 100 is configured for use with an automobile 104. The automobile 104 further comprises a rearview mirror 105. The invention 100 mounts on the anterior face of the rearview mirror 105 such that the invention 100 does not interfere with the operation of the rearview mirror 105. The invention 100 comprises a reservoir 101, a plurality of mirror clips 102, and the cleaning solution 103. The reservoir 101 contains and dispenses the cleaning solution 103. The plurality of mirror clips 102 attach the reservoir 101 to the rearview mirror 105.

The automobile 104 is defined elsewhere in this disclosure. The rearview mirror 105 is defined elsewhere in this disclosure. The client 106 is defined elsewhere in this disclosure. The cleaning solution 103 is defined elsewhere in this disclosure.

The reservoir 101 is a prism-shaped structure. The reservoir 101 is a hollow structure. The reservoir 101 contains the cleaning solution 103. The reservoir 101 receives that cleaning solution 103 for storage. The reservoir 101 dispenses the cleaning solution 103 for use by a client 106. The reservoir 101 is a refillable structure. The reservoir 101 comprises a shell 111, a bladder 112, a plurality of intake structures 113, and a discharge structure 114.

The shell 111 is a roughly prism-shaped structure. The shell 111 has a roughly rectangular block structure. The shell 111 is a rounded structure. The shell 111 is a hollow structure. The shell 111 is a rigid structure. The shell 111 forms a containment space that stores the bladder 112 and the cleaning solution 103. The plurality of mirror clips 102 attaches to the shell 111. The shell 111 is formed with all the apertures and the form factors necessary to allow the shell 111 to accommodate the use and operation of the invention 100. The shell 111 comprises a containment structure 131 and a sight glass 132.

The sight glass 132 is a transparent structure. The sight glass 132 is defined elsewhere in this disclosure. The sight glass 132 installs into the exterior surface of the containment structure 131 such that the fluid level of the cleaning solution 103 within the reservoir 101 is visible from the exterior of the reservoir 101.

The containment structure 131 is a roughly prism-shaped structure. The containment structure 131 has a roughly rectangular block structure. The containment structure 131 is a rounded structure. The containment structure 131 is a hollow structure. The containment structure 131 is a rigid structure. The containment structure 131 forms the containment space that stores the bladder 112 and the cleaning solution 103. The containment structure 131 is formed with all apertures and form factors necessary to allow the containment structure 131 to accommodate the use and operation of the invention 100. The containment structure 131 forms the exterior surfaces of the reservoir 101. The containment structure 131 further comprises an anterior surface 133, a posterior surface 134, a superior surface 135, an inferior surface 136, a starboard lateral surface 137, and a port lateral surface 138.

The anterior surface 133 is the surface of the containment structure 131 that forms the bow of the invention 100. The anterior surface 133 leads the reservoir 101 as the automobile 104 moves in its primary sense of direction. The posterior surface 134 is the surface of the containment structure 131 that forms the stern of the invention 100. The posterior surface 134 is the surface of the reservoir 101 that is distal from the anterior surface 133. The posterior surface 134 forms a non-Euclidean plane. The posterior surface 134 is geometrically similar to the anterior face of the rearview mirror 105. The posterior surface 134 allows the containment structure 131 to sit flush against the rearview mirror 105.

The superior surface 135 is the surface of the reservoir 101 that is proximal to the rearview mirror 105 when the invention 100 mounts on the rearview mirror 105. The superior surface 135 is the surface of the reservoir 101 that has the greatest elevation when attached to the rearview mirror 105. The inferior surface 136 is the surface of the reservoir 101 that is distal from the rearview mirror 105 when the invention mounts on the rearview mirror 105. The inferior surface 136 is the surface of the reservoir 101 that has the lowest elevation when attached to the rearview mirror 105. The inferior surface 136 is the surface of the superior surface 135 of the containment structure 131 that is distal from the superior surface 135. The superior surface 135 further comprises a mirror clip 139

The mirror clip 139 is a clip. The clip is defined elsewhere in this disclosure. The mirror clip 139 mounts on the anterior surface 133 of the containment structure 131. The mirror clip 139 forms a fastening structure that attaches the reservoir 101 to the rearview mirror 105. The mirror clip 139 forms a portion of the load path that transfers the load of the invention 100 to the rearview mirror 105.

The starboard lateral surface 137 is a surface of the containment structure 131 that is roughly perpendicular to each of the anterior surface 133, the posterior surface 134, the superior surface 135, and the inferior surface 136. The starboard lateral surface 137 is proximal to the starboard side of the automobile 104. The port lateral surface 138 is a surface of the containment structure 131 that is roughly perpendicular to each of the anterior surface 133, the posterior surface 134, the superior surface 135, and the inferior surface 136. The port lateral surface 138 is proximal to the port side of the automobile 104. The port lateral surface 138 is the surface of the containment structure 131 that is distal from the starboard lateral surface 137.

The bladder 112 is a flexible structure. The bladder 112 has an elastic nature. The bladder 112 is a fluid impermeable structure. The bladder 112 stores the cleaning solution 103 within the containment structure 131 of the shell 111. The bladder 112 forms the boundaries of the contained space that stores the cleaning solution 103. The bladder 112 is defined elsewhere in this disclosure.

The plurality of intake structures 113 forms a plurality of fluid ports. The fluid port is defined elsewhere in this disclosure. Each of the plurality of intake structures 113 receives the cleaning solution 103. Each of the plurality of intake structures 113 transports the cleaning solution 103 from the exterior of the shell 111 into the bladder 112. The plurality of intake structures 113 comprises a first intake structure 141 and a second intake structure 151.

The first intake structure 141 is a fluid port. The first intake structure 141 receives the cleaning solution 103 into the reservoir 101 for storage. The first intake structure 141 forms a fluid impermeable seal that prevents the cleaning solution 103 from leaking out of the reservoir 101 through the first intake structure 141. The first intake structure 141 secures the cleaning solution 103 within the reservoir 101. The first intake structure 141 comprises a first intake port 142, a first intake cap 143, and a first threaded connection 144.

The first intake port 142 is an aperture that is formed through the superior surface 135 of the containment structure 131. The first intake port 142 forms a fluidic connection between the exterior of the containment structure 131 and the bladder 112 contained within the containment structure 131. The first intake port 142 transports the cleaning solution 103 into the contained space formed by the bladder 112. The first intake cap 143 is a closure that attaches to the first intake port 142. The first intake cap 143 forms the fluid impermeable seal that prevents the cleaning solution 103 from leaking out of the containment structure 131 through the first intake structure 141. The first threaded connection 144 is a fastening structure used to secure the first intake cap 143 to the first intake port 142. The fluid port, the cap, and the threaded connection are defined elsewhere in this disclosure.

The second intake structure 151 is a fluid port. The second intake structure 151 receives the cleaning solution 103 into the reservoir 101 for storage. The second intake structure 151 forms a fluid impermeable seal that prevents the cleaning solution 103 from leaking out of the reservoir 101 through the second intake structure 151. The second intake structure 151 secures the cleaning solution 103 within the reservoir 101. The second intake structure 151 comprises a second intake port 152, a second intake cap 153, and a second threaded connection 154.

The second intake port 152 is an aperture that is formed through the superior surface 135 of the containment structure 131. The second intake port 152 forms a fluidic connection between the exterior of the containment structure 131 and the bladder 112 contained within the containment structure 131. The second intake port 152 transports the cleaning solution 103 into the contained space formed by the bladder 112. The second intake cap 153 is a closure that attaches to the second intake port 152. The second intake cap 153 forms the fluid impermeable seal that prevents the cleaning solution 103 from leaking out of the containment structure 131 through the second intake structure 151. The second threaded connection 154 is a fastening structure used to secure the second intake cap 153 to the second intake port 152. The fluid port, the cap, and the threaded connection are defined elsewhere in this disclosure.

The discharge structure 114 is a mechanical structure. The discharge structure 114 controls the flow of cleaning solution 1003 out of the reservoir 101. The discharge structure 114 releases the cleaning solution 103 into the hand of the client 106. The discharge structure 114 comprises a discharge port 161 and a discharge valve 162.

The discharge port 161 is an aperture that is formed through the inferior surface 136 of the containment structure 131. The discharge port 161 forms a fluidic connection between the exterior of the containment structure 131 and the bladder 112 contained within the containment structure 131. The discharge port 161 transports the cleaning solution 103 into the storage space formed by the bladder 112.

The discharge valve 162 forms the mechanical structure that controls the flow of the cleaning solution 103 as it is discharged from the reservoir 101. The discharge valve 162 is a valve structure that forms a fluid impermeable seal that prevents the inadvertent release of the cleaning solution 103 from the bladder 112 to the exterior of the reservoir 101. The discharge valve 162 installs directly into the discharge port 161. Examples of structures suitable for use as the discharge structure 114 include, but are not limited to, a valve and a universal dispensing pump. The valve and the universal dispensing pump are defined elsewhere in this disclosure.

The plurality of mirror clips 102 forms a fastener. The plurality of mirror clips 102 attaches the reservoir 101 to the rearview mirror 105. The plurality of mirror clips 102 positions the reservoir 101 to the forward side of the rearview mirror 105. Each of the plurality of mirror clips 102 permanently attaches to the reservoir 101. The plurality of mirror clips 102 removably attach the reservoir 101 to the rearview mirror 105. The plurality of mirror clips 102 comprises a first c-clip 121 and a second c-clip 122.

The first c-clip 121 is a c-clip. The c-clip is defined elsewhere in this disclosure. The first c-clip 121 is formed as a U-shaped structure. The first c-clip 121 removably attaches the reservoir 101 to the rearview mirror 105. The first c-clip 121 forms a portion of the load path that transfers the load of the reservoir 101 to the rearview mirror 105. The first c-clip 121 permanently attaches to the shell 111 of the reservoir 101.

The first c-clip 121 acts as a spring. Specifically, when the rearview mirror 105 inserts into the hollow interior of the first c-clip 121 the lateral face of the prism-shaped structure of the first c-clip 121 deforms such in a direction such that the inner diameter of the prism structure of the first c-clip 121 increases. The deformation of the lateral face of the prism-shaped structure of the first c-clip 121 applies a counterforce that attempts to return first c-clip 121 to its original positions. When the rearview mirror 105 inserts into the first c-clip 121, the first c-clip 121 applies a pressure against the rearview mirror 105 that effectively attaches the reservoir 101 to the rearview mirror 105.

The first c-clip 121 comprises a first arm 171, a second arm 172, a first crossbeam 181, and a first screw 191.

The first arm 171 is an arm of the u-shaped structure that forms the first c-clip 121. The first arm 171 attaches to a congruent end of the first crossbeam 181. The first arm 171 attaches to the first crossbeam 181 in the manner of a cantilever. The second arm 172 is an arm of the u-shaped structure that forms the first c-clip 121. The second arm 172 attaches to a first congruent end of the first crossbeam 181 that is distal from the first arm 171. The second arm 172 attaches to the first crossbeam 181 in the manner of a cantilever.

The first arm 171 attaches to the first crossbeam 181 such that the first arm 171 projects perpendicularly away from the first crossbeam 181. The second arm 172 attaches to the first crossbeam 181 such that the second arm 172 projects perpendicularly away from the first crossbeam 181. The second arm 172 attaches to the first crossbeam 181 such that the first arm 171 and the second arm 172 are parallel to each other.

The first crossbeam 181 forms the crossbeam of the u-shaped structure that forms the first c-clip 121. The first arm 171, the second arm 172, and the first crossbeam 181 combine to form a cantilever v spring that clips the invention 100 to the rearview mirror 105. The first screw 191 is a screw. The first screw 191 screws the first crossbeam 181 into the anterior surface 133 of the containment structure 131. The cantilever v spring and the u-shaped structure are defined elsewhere in this disclosure.

The second c-clip 122 is a c-clip. The c-clip is defined elsewhere in this disclosure. The second c-clip 122 is formed as a U-shaped structure. The second c-clip 122 removably attaches the reservoir 101 to the rearview mirror 105. The second c-clip 122 forms a portion of the load path that transfers the load of the reservoir 101 to the rearview mirror 105. The second c-clip 122 permanently attaches to the shell of the reservoir 101.

The second c-clip 122 acts as a spring. Specifically, when the rearview mirror 105 inserts into the hollow interior of the second c-clip 122 the lateral face of the prism-shaped structure of the second c-clip 122 deforms such in a direction such that the inner diameter of the prism structure of the second c-clip 122 increases. The deformation of the lateral face of the prism-shaped structure of the second c-clip 122 applies a counterforce that attempts to return second c-clip 122 to its original positions. When the rearview mirror 105 inserts into the second c-clip 122, the second c-clip 122 applies a pressure against the rearview mirror 105 that effectively attaches the reservoir 101 to the rearview mirror 105.

The second c-clip 122 comprises a third arm 173, a fourth arm 174, a second crossbeam 182, and a second screw 192.

The third arm 173 is an arm of the u-shaped structure that forms the second c-clip 122. The third arm 173 attaches to a congruent end of the second crossbeam 182. The third arm 173 attaches to the second crossbeam 182 in the manner of a cantilever. The fourth arm 174 is an arm of the u-shaped structure that forms the second c-clip 122. The fourth arm 174 attaches to a first congruent end of the second crossbeam 182 that is distal from the third arm 173. The fourth arm 174 attaches to the second crossbeam 182 in the manner of a cantilever.

The third arm 173 attaches to the second crossbeam 182 such that the third arm 173 projects perpendicularly away from the second crossbeam 182. The fourth arm 174 attaches to the second crossbeam 182 such that the fourth arm 174 projects perpendicularly away from the second crossbeam 182. The fourth arm 174 attaches to the second crossbeam 182 such that the third arm 173 and the fourth arm 174 are parallel to each other.

The second crossbeam 182 forms the crossbeam of the u-shaped structure that forms the second c-clip 122. The third arm 173, the fourth arm 174, and the second crossbeam 182 combine to form a cantilever v spring that clips the invention 100 to the rearview mirror 105. The second screw 192 is a screw. The second screw 192 screws the second crossbeam 182 into the anterior surface 133 of the containment structure 131. The cantilever v spring and the u-shaped structure are defined elsewhere in this disclosure.

The following definitions were used in this disclosure:

Aft: As used in this disclosure, aft is term that relates a first object to a second object. When the second object is closer to the stern of a vehicle, the second object is said to be aft of the first object. The term is commonly used on vessels and vehicles.

Alcohol: As used in this disclosure, an alcohol refers to an organic chemical structure that comprises a hydroxyl functional group.

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Anterior: As used in this disclosure, anterior is a term that is used to refer to the front side or direction of a structure. When comparing two objects, the anterior object is the object that is closer to the front of the structure.

Automobile: As used in this disclosure, an automobile is a road vehicle that specializes in carrying passengers and light cargo loads. This definition is specifically intended to include vehicles generally referred to as pickup trucks, vans, minivans, and sport utility vehicles. The automobile further comprises an electrical system. The automobile is further defined with a hood panel and a roof panel. The automobile is often defined with a trunk panel.

Bladder: As used in this disclosure, a bladder is fluid impermeable structure. The internal volume of the structure can be varied by: a) varying the pressure and/or quantity of a fluid contained within the bladder; or b) varying the quantity of a liquid contained within the bladder. Bladders are commonly used for storage of a fluid and as a cushion.

Bow: As used in this disclosure, the bow refers to the anterior side of an object, vehicle, or vessel. Specifically, the bow refers to the most forward element of the object in the direction of the primary sense of direction of the object vehicle, or vessel.

C-Clip: As used in this disclosure, a C-clip is a fastening device that is formed in the shape of a hollow prismatic bifurcation. The congruent ends of the base prism shape that forms the C-clip forms a C shape or a U shape. The lateral face of the base prism shape that forms the C-clip is formed as an elastic structure. When an object is inserted into the hollow interior of the C-clip, a force is applied to the lateral face of the C-clip such that the C-clip the force elastically deforms in a direction that increases the inner diameter of the C-clip.: The C-clip resists the application of the force by attempting to return to its relaxed shape. The C-clip stores the energy deformation such that when the force is no longer applied the cantilever V spring returns to its relaxed shape. This stored energy applies a pressure to the object that secures the object in position within the C-clip. The C-clip is also referred to as a circlip or a snap ring.

Cant: As used in this disclosure, a cant is an angular deviation from one or more reference lines (or planes) such as a vertical line (or plane) or a horizontal line (or plane).

Cantilever: As used in this disclosure, a cantilever is a beam or other structure that projects away from an object and is supported on only one end. A cantilever is further defined with a fixed end and a free end. The fixed end is the end of the cantilever that is attached to the object. The free end is the end of the cantilever that is distal from the fixed end.

Cantilever V Spring: As used in this disclosure, a cantilever V spring is a torsion spring that is formed in a chevron, hyoid, or horseshoe shape. The cantilever V spring comprises a first cantilever structure and a second cantilever structure wherein the fixed end of the first cantilever structure is attached to the fixed end of the second cantilever structure. Within this structure, when a force is applied to the cantilever V spring such that the first cantilever structure moves relative to from the second cantilever structure the force deforms the cantilever V spring in an elastic manner that: 1) resists the application of the force; and 2) stores the energy deformation such that when the force is no longer applied the cantilever V spring returns to its relaxed shape. Depending on the application, a cantilever V spring can be considered a torsion spring, a tension spring, or a compression spring. The term offset cantilever V spring means that the span of the length of the first cantilever structure differs from the span of the length of the second cantilever structure.

Cap: As used in this disclosure, a cap is a protective cover that encloses a space or opening.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Clean: As used in this disclosure, the term clean refers to an object without dirt, unwanted markings, or undesirable pathogens. When referring to a surface, the term clean can also refer to removing unwanted objects from the surface. The term cleaning refers to the action of making an object clean.

Cleaning Agent: As used in this disclosure, a cleaning agent is a chemical compound used to remove dirt and detritus from a surface.

Cleaning Solution: As used in this disclosure, a cleaning solution is a chemical solution that contains a solvent used to dissolve and capture dirt and detritus from a surface. The cleaning solution often contains a cleaning agent.

Client: As used in this disclosure, a client is an individual who is designated to receive a service.

Clip: As used in this disclosure, a clip is a fastener that attaches to an object by gripping or clasping the object. A clip is typically spring loaded.

Composite Prism: As used in this disclosure, a composite prism refers to a structure that is formed from a plurality of structures selected from the group consisting of a prism structure and a pyramid structure. The plurality of selected structures may or may not be truncated. The plurality of prism structures are joined together such that the center axes of each of the plurality of structures are aligned. The congruent ends of any two structures selected from the group consisting of a prism structure and a pyramid structure need not be geometrically similar.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Correspond: As used in this disclosure, the term correspond is used as a comparison between two or more objects wherein one or more properties shared by the two or more objects match, agree, or align within acceptable manufacturing tolerances.

Disinfectant: As used in this disclosure, a disinfectant is a chemical that destroys or inhibits the activities of pathogenic microorganisms.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Drape: As used in this disclosure, to drape means to suspend a sheeting.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Elastic Nature: As used in this disclosure, an elastic nature refers to a flexible structure that returns to its relaxed shape after the flexible structure has been deformed.

Elevation: As used in this disclosure, elevation refers to the span of the distance in the superior direction between a specified horizontal surface and a reference horizontal surface. Unless the context of the disclosure suggest otherwise, the specified horizontal surface is the supporting surface the potential embodiment of the disclosure rests on. The infinitive form of elevation is to elevate.

Exterior: As used in this disclosure, the exterior is used as a relational term that implies that an object is not contained within the boundary of a structure or a space.

Fastener: As used in this disclosure, a fastener is a device that is used to removably attach a first object to a second object.

Flexible: As used in this disclosure, flexible refers to an object or material that will deform when a force is applied to it but that will not necessarily return to its original shape when the deforming force is removed.

Fluid: As used in this disclosure, a fluid refers to a state of matter wherein the matter is capable of flow and takes the shape of a container it is placed within. The term fluid commonly refers to a liquid or a gas.

Fluid Port: As used in this disclosure, a fluid port is an opening formed in an object that allows fluid to flow through the boundary of the object.

Flush: As used in this disclosure, the term flush is used to describe the alignment of a first surface and a second surface to form a single structure selected from the group consisting of a Euclidean plane and a non-Euclidean plane.

Force of Gravity: As used in this disclosure, the force of gravity refers to a vector that indicates the direction of the pull of gravity on an object at or near the surface of the earth.

Form Factor: As used in this disclosure, the term form factor refers to the size and shape of an object.

Forward: As used in this disclosure, forward is term that relates a first object to a second object. When the first object is closer to the bow of a vehicle, the first object is said to be forward of the second object. The term is commonly used on vessels and vehicles. See bow, aft, port, starboard, and stern Gas: As used in this disclosure, a gas refers to a state (phase) of matter that is fluid and that fills the volume of the structure that contains it. Stated differently, the volume of a gas always equals the volume of its container.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Horizontal: As used in this disclosure, horizontal is a directional term that refers to a direction that is either: 1) parallel to the horizon; 2) perpendicular to the local force of gravity, or, 3) parallel to a supporting surface. In cases where the appropriate definition or definitions are not obvious, the second option should be used in interpreting the specification. Unless specifically noted in this disclosure, the horizontal direction is always perpendicular to the vertical direction.

Inelastic Nature: As used in this disclosure, an inelastic nature refers to a flexible structure that maintains its new shape after the flexible structure has been deformed.

Inferior: As used in this disclosure, the term inferior refers to a directional reference that is parallel to and in the same direction as the force of gravity when an object is positioned or used normally.

Interior: As used in this disclosure, the interior is used as a relational term that implies that an object is contained within the boundary of a structure or a space.

Lateral: As used in this disclosure, the term lateral refers to the movement of an object that is perpendicular to the primary sense of direction of an object and parallel to the horizontal plane (or perpendicular to the vertical plane). Lateral movement is always perpendicular to the anterior posterior axis. Lateral movement is often called sideways movement.

Liquid: As used in this disclosure, a liquid refers to a state (phase) of matter that is fluid and that maintains, for a given pressure, a fixed volume that is independent of the volume of the container.

Microorganism: As used in this disclosure, a microorganism is an organism too small to be viewed by the unaided eye. Microorganisms are typically single celled organisms such as bacteria, yeast, viruses, protozoa, fungi and algae. A pathogen refers to a microorganism that has the potential to cause illness or disease.

Mirror: As used in this disclosure, a mirror is a surface that is designed to reflect light with a minimum of dispersion or absorption. A mirror may or may not be formed with curved surfaces that are used to concentrate or disperse the light that reflects off the mirror. See half-silvered Negative Space: As used in this disclosure, negative space is a method of defining an object through the use of open or empty space as the definition of the object itself, or, through the use of open or empty space to describe the boundaries of an object.

Non-Polar Molecule: As used in this disclosure, a non-polar molecule refers to a molecular structure that: a) is electrically neutral; and, b) has a uniform spatial distribution of the electrons within the molecule.

Non-Euclidean Plane: As used in this disclosure, a non-Euclidean plane is a geometric plane that is formed with a curvature such that: a) two parallel lines will intersect somewhere in the planar surface; or, b) the span of the perpendicular distance between two parallel lines will vary as a function of the position of the plane. In many geometries, the statements (a) and (b) can be considered identical statements. A non-Euclidean plane (or surface) is said to form a roughly Euclidean plane (or surface) when the span of the minimum distance between two points on the non-Euclidean plane as measured along the non-Euclidean plane is less than or equal to 1.1 times the absolute minimum distance between the same two points.

Non-Euclidean Structure: As used in this disclosure, a non-Euclidean structure is a structure wherein an axis of the structure lies on a non-Euclidean plane or is otherwise formed with a curvature.

Not Significantly Different: As used in this disclosure, the term not significantly different compares a specified property of a first object to the corresponding property of a reference object (reference property). The specified property is considered to be not significantly different from the reference property when the absolute value of the difference between the specified property and the reference property is less than 10.0% of the reference property value. A negligible difference is considered to be not significantly different One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Perimeter: As used in this disclosure, a perimeter is one or more curved or straight lines that bounds an enclosed area on a plane or surface. The perimeter of a circle is commonly referred to as a circumference.

Polar Molecule: As used in this disclosure, a polar molecule refers to a molecular structure that: a) is electrically neutral; but, b) does not have a uniform spatial distribution of the electrons within the molecule. A polar molecule will present one or more electrically positive poles and the same number of electrically negative poles within the molecular structure.

Polarity: As used in this disclosure, the term polarity is used to describe a physical property or physical characteristic wherein: 1) the physical property or physical characteristic manifests two opposing attributes, tendencies, characteristics, or principals; and, 2) the two opposing attributes, tendencies, characteristics, or principals have an intrinsic separation, alignment, or orientation.

Port: As used in this disclosure, port refers to the left side of a vehicle when a viewer is facing towards the primary sense of direction of the vehicle.

Port: As used in this disclosure, a port is an aperture formed in an object that allows fluid to flow through the boundary of the object.

Posterior: As used in this disclosure, posterior is a term that is used to refer to the side of an object that is distal or in the opposite direction of the anterior side. When comparing two items, the posterior item is the item that is distal from the anterior of the object.

Primary Sense of Direction: As used in this disclosure, the primary sense of direction of an object refers to a vector that: 1) passes through the center of the object; and, 2) is parallel to the direction of travel when the anterior surface(s) of the object are leading the object into the direction of travel. This definition intends to align with what people would normally call the forward direction of an object.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Pump: As used in this disclosure, a pump is a mechanical device that uses suction or pressure to raise or move fluids, compress fluids, or force a fluid into an inflatable object. Within this disclosure, a compressor refers to a pump that is dedicated to compressing a fluid or placing a fluid under pressure.

Rearview Mirror: As used in this disclosure, a rearview mirror is a mirror configured for use with a vehicle. The rearview mounts on the anterior (commonly referred to as the front) windshield of the vehicle such that the operator of the vehicle can look into the rearview mirror to see through the posterior (commonly referred to as the rear) windshield.

Rectangular Block: As used in this disclosure, a rectangular block refers to a three-dimensional prism structure comprising six rectangular surfaces (commonly called faces) formed at right angles. Within this disclosure, a rectangular block may further comprise rounded edges and corners.

Relaxed Shape: As used in this disclosure, a structure is considered to be in its relaxed state when no shear, strain, or torsional forces are being applied to the structure.

Reservoir: As used in this disclosure, a reservoir refers to a container or containment system that is configured to store a liquid.

Rigid Structure: As used in this disclosure, a rigid structure is a solid structure formed from an inelastic material that resists changes in shape. A rigid structure will permanently deform as it fails under a force. See bimodal flexible structure.

Roughly: As used in this disclosure, roughly refers to a comparison between two objects. Roughly means that the difference between one or more parameters of the two compared objects are not significantly different.

Rounded: A used in this disclosure, the term rounded refers to the replacement of an apex, vertex, or edge or brink of a structure with a (generally smooth) curvature wherein the concave portion of the curvature faces the interior or center of the structure.

Screw: As used in this disclosure, to screw is a verb meaning: 1) to fasten or unfasten (unscrew) a threaded connection; or 2) to attach a helical structure to a solid structure.

Screw: As used in this disclosure, a screw is a cylindrical, or tapered cylindrical, structure that is formed with an exterior screw thread. A screw is used to attach a first object to a second object. Screws are well known and documented in the mechanical arts.

Semi-Rigid Structure: As used in this disclosure, a semi-rigid structure is a solid structure that is stiff but not wholly inflexible and that will deform under force before breaking. A semi-rigid structure may or may not behave with an elastic nature in that a semi-rigid structure need not return to its relaxed shape.

Sheeting: As used in this disclosure, a sheeting is a material, such as a paper, textile, a plastic, or a metal foil, in the form of a thin flexible layer or layers. The sheeting forms a disk structure. The two surfaces of the sheeting with the greatest surface area are called the faces of the sheeting.

Sight Glass: As used in this disclosure, a sight glass is a transparent structure that allows a user to see the level of a liquid within a container. A sight glass may or may not be calibrated to measure the volume of liquid within the container.

Solution: As used in this disclosure, a solution is a uniform mixture of two or more compounds in a liquid phase. The major component selected from the two or more compounds that forms the solution is called the solvent. The components remaining in the two or more compounds are called the solute. A polar solvent is a solvent formed from polar molecules. A non-polar solvent is a solvent formed from non-polar molecules. The rule of thumb that "like dissolves like" states that: a) solutes formed from polar molecules will dissolve in polar solvents but will not dissolve in non-polar solvents; and, b) solutes formed from non-polar molecules will dissolve in non-polar solvents but will not dissolve in polar solvents.

Spring: As used in this disclosure, a spring is a device that is used to store mechanical energy. This mechanical energy will often be stored by: 1) deforming an elastomeric material that is used to make the device; 2) the application of a torque to a semi-rigid structure; or 3) a combination of the previous two items.

Starboard: As used in this disclosure, starboard refers to the right side of a vehicle when a viewer is facing towards the primary sense of direction of the vehicle.

Stern: As used in this disclosure, the stern refers to the posterior side of an object, vehicle, or vessel. The stern is distal from the bow along the primary sense of direction.

Superior: As used in this disclosure, the term superior refers to a directional reference that is parallel to and in the opposite direction of the force of gravity when an object is positioned or used normally.

Suspend: As used in this disclosure, to suspend an object means to support an object such that the inferior end of the object does not form a significant portion of the load path of the object.

Threaded Connection: As used in this disclosure, a threaded connection is a type of fastener that is used to join a first cylindrical object and a second cylindrical object together. The first cylindrical object is fitted with a first fitting selected from an interior screw thread or an exterior screw thread. The second cylindrical object is fitted with the remaining screw thread. The cylindrical object fitted with the exterior screw thread is placed into the remaining cylindrical object such that: 1) the interior screw thread and the exterior screw thread interconnect; and, 2) when the cylindrical object fitted with the exterior screw thread is rotated the rotational motion is converted into linear motion that moves the cylindrical object fitted with the exterior screw thread either into or out of the remaining cylindrical object. The direction of linear motion is determined by the direction of rotation.

Transparent: As used in this disclosure, transparent refers to a material that allows light to pass through the material without significant scattering such that an object can be clearly seen through the material. Universal Dispenser Pump: As used in this disclosure, a universal dispenser pump is a pump that is used to pump a liquid out of a bottle. The universal dispenser pump is a well-known and documented commercially available product that is often referred to as a soap pump or a shampoo pump.

U-Shaped Structure: As used in this disclosure, a U-shaped structure refers to a three-sided structure comprising a crossbeam, a first arm, and a second arm. In a U-shaped structure, the first arm and the second arm project away from the crossbeam: 1) in the same direction; 2) at a roughly perpendicular angle to the crossbeam, and, 3) the span of the length of the first arm roughly equals the span of the length of the second arm. The first arm and the second arm project away from the crossbeam in the manner of a cantilever.

Valve: As used in this disclosure, a valve is a device that is used to control the flow of a fluid (gas or liquid) through a pipe, tube, or hose.

Vehicle: As used in this disclosure, a vehicle is a motorized device that is used for transporting passengers, goods, or equipment. The term motorized vehicle refers to a vehicle that can move under power provided by an electric motor or an internal combustion engine.

Vertical: As used in this disclosure, vertical refers to a direction that is either: 1) perpendicular to the horizontal direction; 2) parallel to the local force of gravity; or, 3) when referring to an individual object the direction from the designated top of the individual object to the designated bottom of the individual object. In cases where the appropriate definition or definitions are not obvious, the second option should be used in interpreting the specification. Unless specifically noted in this disclosure, the vertical direction is always perpendicular to the horizontal direction.

With respect to the above description, it is to be realized that the optimum dimensional relationship for the various components of the invention described above and in FIGS. 1 through 6 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A vehicle sanitizer dispenser comprising
a reservoir, a plurality of mirror clips, and the cleaning solution;
wherein the reservoir contains and dispenses the cleaning solution;
wherein the plurality of mirror clips attach the reservoir to the rearview mirror;
wherein the vehicle sanitizer dispenser is a mechanical structure;
wherein the vehicle sanitizer dispenser is configured for use with a cleaning solution;
wherein the vehicle sanitizer dispenser is configured for use with an automobile;
wherein the automobile further comprises a rearview mirror;
wherein the vehicle sanitizer dispenser mounts on the anterior face of the rearview mirror such that the vehicle sanitizer dispenser does not interfere with the operation of the rearview mirror.

2. The vehicle sanitizer dispenser according to claim 1
wherein the reservoir is a hollow structure;
wherein the reservoir contains the cleaning solution;
wherein the reservoir receives that cleaning solution for storage;
wherein the reservoir dispenses the cleaning solution for use by a client;
wherein the reservoir is a refillable structure.

3. The vehicle sanitizer dispenser according to claim 2
wherein the plurality of mirror clips forms a fastener;
wherein the plurality of mirror clips attaches the reservoir to the rearview mirror;
wherein the plurality of mirror clips positions the reservoir to the forward side of the rearview mirror;
wherein each of the plurality of mirror clips permanently attaches to the reservoir;
wherein the plurality of mirror clips removably attach the reservoir to the rearview mirror.

4. The vehicle sanitizer dispenser according to claim 3
wherein the reservoir comprises a shell, a bladder, a plurality of intake structures, and a discharge structure;
wherein the shell forms a containment space that stores the bladder and the cleaning solution;
wherein the bladder stores the cleaning solution within the containment structure of the shell;
wherein each of the plurality of intake structures transports the cleaning solution from the exterior of the shell into the bladder;
wherein the discharge structure is a mechanical structure;
wherein the discharge structure controls the flow of cleaning solution out of the reservoir.

5. The vehicle sanitizer dispenser according to claim 4
wherein the plurality of mirror clips comprises a first c-clip and a second c-clip;
wherein the first c-clip removably attaches the reservoir to the rearview mirror;
wherein the first c-clip forms a portion of the load path that transfers the load of the reservoir to the rearview mirror;
wherein the second c-clip removably attaches the reservoir to the rearview mirror;
wherein the second c-clip forms a portion of the load path that transfers the load of the reservoir to the rearview mirror.

6. The vehicle sanitizer dispenser according to claim 5
wherein the shell is a roughly prism-shaped structure;
wherein the shell has a roughly rectangular block structure;
wherein the shell is a rounded structure;
wherein the shell is a hollow structure;
wherein the shell is a rigid structure;
wherein the plurality of mirror clips attaches to the shell.

7. The vehicle sanitizer dispenser according to claim 6
wherein the shell comprises a containment structure and a sight glass;
wherein the sight glass is a transparent structure;
wherein the sight glass installs into the exterior surface of the containment structure such that the fluid level of the cleaning solution within the reservoir is visible from the exterior of the reservoir.

8. The vehicle sanitizer dispenser according to claim 7
wherein the containment structure has a roughly rectangular block structure;
wherein the containment structure is a rounded structure;
wherein the containment structure is a hollow structure;
wherein the containment structure is a rigid structure;
wherein the containment structure forms the containment space that stores the bladder and the cleaning solution;
wherein the containment structure forms the exterior surfaces of the reservoir.

9. The vehicle sanitizer dispenser according to claim 8
wherein the containment structure further comprises an anterior surface, a posterior surface, a superior surface, an inferior surface, a starboard lateral surface, and a port lateral surface;
wherein the anterior surface is the surface of the containment structure that forms the bow of the vehicle sanitizer dispenser;
wherein the anterior surface leads the reservoir as the automobile moves in its primary sense of direction;
wherein the posterior surface is the surface of the containment structure that forms the stern of the vehicle sanitizer dispenser;
wherein the posterior surface is the surface of the reservoir that is distal from the anterior surface;
wherein the posterior surface forms a non-Euclidean plane;
wherein the posterior surface is geometrically similar to the anterior face of the rearview mirror;
wherein the posterior surface allows the containment structure to sit flush against the rearview mirror;
wherein the superior surface is the surface of the reservoir that is proximal to the rearview mirror when the vehicle sanitizer dispenser mounts on the rearview mirror;
wherein the superior surface is the surface of the reservoir that has the greatest elevation when attached to the rearview mirror;
wherein the inferior surface is the surface of the reservoir that is distal from the rearview mirror when the vehicle sanitizer dispenser mounts on the rearview mirror;
wherein the inferior surface is the surface of the reservoir that has the lowest elevation when attached to the rearview mirror;
wherein the inferior surface is the surface of the superior surface of the containment structure that is distal from the superior surface;
wherein the starboard lateral surface is a surface of the containment structure that is roughly perpendicular to each of the anterior surface, the posterior surface, the superior surface, and the inferior surface;
wherein the starboard lateral surface is proximal to the starboard side of the automobile;
wherein the port lateral surface is a surface of the containment structure that is roughly perpendicular to each of the anterior surface, the posterior surface, the superior surface, and the inferior surface;
wherein the port lateral surface is proximal to the port side of the automobile;
wherein the port lateral surface is the surface of the containment structure that is distal from the starboard lateral surface.

10. The vehicle sanitizer dispenser according to claim 9 wherein the superior surface further comprises a mirror clip
the mirror clip is a clip;
wherein the mirror clip mounts on the anterior surface of the containment structure;
wherein the mirror clip forms a fastening structure that attaches the reservoir to the rearview mirror;
wherein the mirror clip forms a portion of the load path that transfers the load of the vehicle sanitizer dispenser to the rearview mirror.

11. The vehicle sanitizer dispenser according to claim 10 wherein the bladder is a flexible structure;
wherein the bladder has an elastic nature;
wherein the bladder is a fluid impermeable structure;
wherein the bladder forms the boundaries of the contained space that stores the cleaning solution.

12. The vehicle sanitizer dispenser according to claim 11 wherein the plurality of intake structures comprises a first intake structure and a second intake structure;
wherein the first intake structure is a fluid port;
wherein the first intake structure receives the cleaning solution into the reservoir for storage;
wherein the first intake structure forms a fluid impermeable seal that prevents the cleaning solution from leaking out of the reservoir through the first intake structure;
wherein the first intake structure secures the cleaning solution within the reservoir;
wherein the second intake structure is a fluid port;
wherein the second intake structure receives the cleaning solution into the reservoir for storage;
wherein the second intake structure forms a fluid impermeable seal that prevents the cleaning solution from leaking out of the reservoir through the second intake structure;
wherein the second intake structure secures the cleaning solution within the reservoir.

13. The vehicle sanitizer dispenser according to claim 12 wherein the first intake structure comprises a first intake port, a first intake cap, and a first threaded connection;
wherein the first intake port is an aperture that is formed through the superior surface of the containment structure;
wherein the first intake port forms a fluidic connection between the exterior of the containment structure and the bladder contained within the containment structure;
wherein the first intake port transports the cleaning solution into the contained space formed by the bladder;
wherein the first intake cap is a closure that attaches to the first intake port;
wherein the first intake cap forms the fluid impermeable seal that prevents the cleaning solution from leaking out of the containment structure through the first intake structure;
wherein the first threaded connection is a fastening structure used to secure the first intake cap to the first intake port.

14. The vehicle sanitizer dispenser according to claim 13 wherein the second intake structure comprises a second intake port, a second intake cap, and a second threaded connection;
wherein the second intake port is an aperture that is formed through the superior surface of the containment structure;
wherein the second intake port forms a fluidic connection between the exterior of the containment structure and the bladder contained within the containment structure;
wherein the second intake port transports the cleaning solution into the contained space formed by the bladder;
wherein the second intake cap is a closure that attaches to the second intake port;
wherein the second intake cap forms the fluid impermeable seal that prevents the cleaning solution from leaking out of the containment structure through the second intake structure;
wherein the second threaded connection is a fastening structure used to secure the second intake cap to the second intake port.

15. The vehicle sanitizer dispenser according to claim 14 wherein the discharge structure comprises a discharge port and a discharge valve;
wherein the discharge port is an aperture that is formed through the inferior surface of the containment structure;
wherein the discharge port forms a fluidic connection between the exterior of the containment structure and the bladder contained within the containment structure;
wherein the discharge port transports the cleaning solution into the storage space formed by the bladder;
wherein the discharge valve forms the mechanical structure that controls the flow of the cleaning solution as the cleaning solution is discharged from the reservoir;
wherein the discharge valve is a valve structure that forms a fluid impermeable seal that prevents the inadvertent release of the cleaning solution from the bladder to the exterior of the reservoir;
wherein the discharge valve installs directly into the discharge port.

16. The vehicle sanitizer dispenser according to claim 15 wherein the first c-clip is a c-clip;
wherein the first c-clip is formed as a u-shaped structure;
wherein the first c-clip permanently attaches to the shell of the reservoir;
wherein the first c-clip acts as a spring;
wherein the first c-clip attaches the vehicle sanitizer dispenser to the rearview mirror;
wherein the second c-clip is a c-clip;
wherein the second c-clip is formed as a u-shaped structure;
wherein the second c-clip permanently attaches to the shell of the reservoir;
wherein the second c-clip acts as a spring;
wherein the second c-clip, the second c-clip attaches the vehicle sanitizer dispenser to the rearview mirror.

17. The vehicle sanitizer dispenser according to claim 16
wherein the first c-clip comprises a first arm, a second arm, a first crossbeam, and a first screw;
wherein the second c-clip comprises a third arm, a fourth arm, a second crossbeam, and a second screw;
wherein the first arm, the second arm, and the first crossbeam combine to form a cantilever v spring that clips the vehicle sanitizer dispenser to the rearview mirror;
wherein the first screw is a screw;
wherein the first screw screws the first crossbeam into the anterior surface of the containment structure;
wherein the third arm, the fourth arm, and the second crossbeam combine to form a cantilever v spring that clips the vehicle sanitizer dispenser to the rearview mirror;
wherein the second screw is a screw;
wherein the second screw screws the second crossbeam into the anterior surface of the containment structure.

18. The vehicle sanitizer dispenser according to claim 17
wherein the first crossbeam forms the crossbeam of the u-shaped structure that forms the first c-clip;
wherein the second crossbeam forms the crossbeam of the u-shaped structure that forms the second c-clip;
wherein the first arm is an arm of the u-shaped structure that forms the first c-clip;
wherein the first arm attaches to a congruent end of the first crossbeam;
wherein the first arm attaches to the first crossbeam in the manner of a cantilever;
wherein the second arm is an arm of the u-shaped structure that forms the first c-clip;
wherein the second arm attaches to the congruent end of the first crossbeam that is distal from the first arm;
wherein the second arm attaches to the first crossbeam in the manner of a cantilever;
wherein the third arm is an arm of the u-shaped structure that forms the second c-clip;
wherein the third arm attaches to a congruent end of the second crossbeam;
wherein the third arm attaches to the second crossbeam in the manner of a cantilever;
wherein the fourth arm is an arm of the u-shaped structure that forms the second c-clip;
wherein the fourth arm attaches to a first congruent end of the second crossbeam that is distal from the third arm;
wherein the fourth arm attaches to the second crossbeam in the manner of a cantilever.

19. The vehicle sanitizer dispenser according to claim 18
wherein the first arm attaches to the first crossbeam such that the first arm projects perpendicularly away from the first crossbeam;
wherein the second arm attaches to the first crossbeam such that the second arm projects perpendicularly away from the first crossbeam;
wherein the third arm attaches to the second crossbeam such that the third arm projects perpendicularly away from the second crossbeam;
wherein the fourth arm attaches to the second crossbeam such that the fourth arm projects perpendicularly away from the second crossbeam.

20. The vehicle sanitizer dispenser according to claim 19
wherein the second arm attaches to the first crossbeam such that the first arm and the second arm are parallel to each other;
wherein the fourth arm attaches to the second crossbeam such that the third arm and the fourth arm are parallel to each other.

* * * * *